United States Patent

Selker et al.

Patent Number: 6,067,466
Date of Patent: May 23, 2000

[54] DIAGNOSTIC TOOL USING A PREDICTIVE INSTRUMENT

[75] Inventors: Harry P. Selker, Wellesley; John L. Griffith, Natick; Joni R. Beshansky, Wayland, all of Mass.

[73] Assignee: New England Medical Center Hospitals, Inc., Boston, Mass.

[21] Appl. No.: 09/193,971

[22] Filed: Nov. 18, 1998

[51] Int. Cl.[7] .................................................. A61B 5/0402
[52] U.S. Cl. .......................................... 600/513; 600/515
[58] Field of Search ................................. 600/300, 301, 600/509, 513, 515, 516, 517

[56] References Cited

U.S. PATENT DOCUMENTS

| | | | |
|---|---|---|---|
| 4,957,115 | 9/1990 | Selker | 600/509 |
| 4,998,535 | 3/1991 | Selker et al. | 600/509 |
| 5,398,886 | 3/1995 | Cuypers | 600/301 |
| 5,501,229 | 3/1996 | Selker et al. | 600/508 |

*Primary Examiner*—Kennedy J. Schaetzle
*Attorney, Agent, or Firm*—Fish & Richardson P.C.

[57] ABSTRACT

A method for evaluating a medical condition of a patient including the steps of monitoring one or more clinical features of a patient; based on the monitored features, computing a primary probability of a medical outcome or diagnosis; computing a plurality of conditional probabilities for a selected diagnostic test, the computed conditional probabilities including a first probability of the medical outcome or diagnosis assuming the selected diagnostic test produces a first outcome and a second probability of the medical outcome or diagnosis assuming the selected diagnostic test produces a second outcome; and displaying the computed primary probability as well as the plurality of computed conditional probabilities to a user as an aid to determining whether to administer the selected diagnostic test to the patient.

6 Claims, 4 Drawing Sheets

| Variable | Coefficients (bi) | | Values $(X_i)^a$ |
|---|---|---|---|
| CONSTANT $(b_0)$ CPAIN | -3.933 1.231 | chest of left arm pain/pressure present not present | 1 0 |
| SX1CPAIN | 0.882 | chest of left arm pain chief complaint otherwise | 1 0 |
| MALESEX | 0.712 | male female | 1 0 |
| AGE 40 | -1.441 | patient age 40 yrs or less otherwise | 1 0 |
| AGE 50 | 0.667 | patient age greater than 50 yrs otherwise | 1 0 |
| SEXAGE50 | -0.426 | male patient age greater than 50 yrs otherwise | 1 0 |
| QWAVE | 0.616 | ECG Q waves present otherwise | 1 0 |
| STEL | 1.314 | ECG S-T segment elevated 2mm or more ECG S-T segment elevated 1-2mm otherwise | 2 1 0 |
| STDEP | 0.993 | ECG S-T segment depressed 2mm or more ECG S-T segment depressed 1-2mm ECG S-T segment depressed 0.5-1.0mm otherwise | 2 1 0.5 0 |
| TWEL | 1.095 | ECG T-waves elevated ("hyperacute) otherwise | 1 0 |
| TWINV | 1.127 | ECG T- waves inverted 5mm or more ECG T- waves inverted 1-5mm ECG T- waves flat otherwise | 2 1 0.5 0 |
| TWISTDEP | -0.314 | <u>Both</u> STDEP and TWINV not 0 otherwise | 1 0 |

FIG. 3

| Variable $x_1$ | Definition | Coefficient ($\beta_1$) |
|---|---|---|
| CHPAIN | =1 chest pain present<br>=0 not present | 0.7006 |
| SX1CP | =1 chest pain primary complaint<br>=0 not primary complaint | 1.5857 |
| GENDER | =1 female<br>=2 male | -0.2329 |
| QWAVES | =1 ECG Q waves present | 0.7665 |
| STDEP | =2 ECG S-T segment depression 2 mm or more<br>=1 ECG S-T segment depression 1-2 mm<br>=0.5 ECG S-T segment depression 0.5-1.0 mm<br>=0 otherwise | 0.5953 |
| STEL | =2 ECG S-T segment elevation 2 mm or more<br>=1 ECG S-T segment elevation 1-2 mm<br>=0 otherwise | 0.5481 |
| TWINV | =2 ECG T- waves inverted 5 mm or more<br>=1 ECG T- waves inverted 1-5 mm<br>=0.5 ECG T- waves inverted 0.5-1 mm<br>=0 otherwise | 0.5163 |
| TWEL | =1 ECG T- waves elevated ("hyperacute") | 0.9880 |
| AGELT60 | =40 for ages less than 40<br>=age -40 for age 40 to 60<br>=20 for ages greater than 60 | 0.0836 |
| AGEGT60 | =0 for ages less than 60<br>=age -60 for ages 60 or greater | 0.0191 |
| CKABN | =1 abnormal CK readings<br>=0 otherwise | 1.7708 |
| Intercept | =1 | -4.5597 |

FIG. 4

DIAGNOSTIC TOOL USING A PREDICTIVE INSTRUMENT

BACKGROUND OF THE INVENTION

The invention relates to predictive instruments or computing a patient's probability of a serious medical condition.

A number of instruments have been developed that enable the physician to compute probabilities of life threatening cardiac conditions for patients. Some of these instruments are described in the following references, all of which are incorporated herein be reference.

A hand-held predictive instrument is described by Michael W. Pozen et al. in "A Predictive Instrument to Improve Coronary-Care-Unit Admission Practices in Acute Ischemic Heart Disease" The New England Journal of Medicine, Vol 310 pp. 1273–1278, May 17, 1984. With the handheld calculator-based instrument, a physician can compute a patient's probability of having acute cardiac ischemia based upon physician-entered values for a set of clinical variables. An automatic, computerized version of this instrument which utilizes output from a electrocardiograph and a waveform analyzer is described by H. P. Selker et al. in "TA Time-Insensitive Predictive Instrument for Acute Myocardial Infarction Mortality", Med. Care 1991; 29:1196–1211.

A predictive instrument for determining the probability of acute hospital mortality of a cardiac patient is described in U.S. Pat. No. 4,957,115 to Dr. Harry P. Selker, and incorporated herein by reference. The probability of acute hospital mortality is commonly understood to mean the probability of dying from a current acute condition, generally during the specific initial hospitalization for the problem. It is also referred to as the probability of imminent death for the patient. That is, it is a short term, as opposed to a long term, probability of mortality which does not necessarily have a precisely defined period of time associated with it.

A predictive instrument for evaluating whether to use thrombolytic therapy to treat a patient with a heart condition is described in U.S. Pat. No. 4,998,535 to Dr. Selker et al., and incorporated herein by reference. The predictive instrument computes a first probability of acute hospital mortality for the patient assuming that thrombolytic therapy is not administered and it computes a second probability of acute hospital mortality for the patient assuming that thrombolytic therapy is administered. The difference in the computed probabilities may assist the physician in deciding whether it would be advantageous to administer the thrombolytic therapy to the patient.

The above-mentioned predictive instruments use logistic regression equations to model the probability that the patient has a serious cardiac condition (e.g. the probability of acute cardiac ischemia or the probability of imminent death from a cardiac condition).

SUMMARY OF THE INVENTION

In general, in one aspect, the invention is a method for evaluating a medical condition of a patient. The method includes the steps of monitoring one or more clinical features of a patient; based on the monitored features, computing a primary probability of a medical outcome or diagnosis; computing a plurality of conditional probabilities for a selected diagnostic test, wherein the conditional probabilities include a first probability of the medical outcome or diagnosis assuming the selected diagnostic test produces a first outcome and a second probability of the medical outcome or diagnosis assuming the selected diagnostic test produces a second outcome; and displaying the computed primary probability as well as the plurality of computed conditional probabilities to a user as an aid to determining whether to administer the selected diagnostic test to the patient.

Preferred embodiments include the following features. The step of monitoring involves monitoring EKG-related characteristics of the patient, wherein the computed primary probability is a probability of a cardiac problem, and wherein the selected diagnostic test is selected from the group consisting of a CK blood test, an ETT, a stress test, and Sestamibi scanning test. The method also includes the step of computing a second plurality of conditional probabilities for a second selected diagnostic test, the second conditional probabilities including a first probability of the medical outcome or diagnosis assuming the second selected diagnostic test produces a first outcome and a second probability of the medical outcome or diagnosis assuming the second selected diagnostic test produces a second outcome. Alternatively and/or in addition, the method includes computing a second plurality of conditional probabilities for a second selected diagnostic test, the second plurality of conditional probabilities assuming a particular outcome of the first-mentioned selected diagnostic test, the second conditional probabilities including a first probability of the medical outcome or diagnosis also assuming the second selected diagnostic test produces a first outcome and a second probability of the medical outcome or diagnosis also assuming the second selected diagnostic test produces a second outcome.

In general, in another aspect, the invention is a method for determining a diagnostic test plan for a patient which includes the steps of: monitoring EKG-related characteristics of the patient; based on the measured characteristics, computing a primary probability of a cardiac problem; computing a plurality of conditional probabilities for a selected diagnostic test, wherein the conditional probabilities include a first probability of cardiac problem assuming the selected diagnostic test produces a first outcome and a second probability assuming the selected diagnostic test produces a second outcome; and displaying the computed primary probability as well as the plurality of computed conditional probabilities to a user as an aid to determining whether to administer the selected diagnostic test to the patient.

In general, in yet another aspect, the invention is a diagnostic apparatus for use with a patient. The apparatus includes a monitoring device which during use monitors one or more clinical features of the patient; an output device; and a predictive instrument receiving input from the monitoring device and programmed to: (1) compute therefrom a primary probability of a medical outcome or diagnosis based on the monitored one or more clinical features; (2) compute a plurality of conditional probabilities for a selected diagnostic test, the plurality of conditional probabilities including a first probability of said medical outcome or diagnosis assuming the selected diagnostic test produces a first outcome and a second probability of said medical outcome or diagnosis assuming the selected diagnostic test produces a second outcome; and (3) display the computed primary probability along with the plurality of computed conditional probabilities on the output device.

The array of computed probabilities not only gives potentially revised probabilities of a diagnostic problem/outcome (e.g. acute ischemia) once the diagnostic test results are in-hand, but more importantly,by providing estimates of the potential probabilities that would result based on the possible results of a particular diagnostic test, it also gives the clinician accurate advice and guidance as to which of the diagnostic tests would be most helpful in diagnosing the seriousness of patient's condition.

Other advantages and features will become apparent from the following description of the preferred embodiment and from the claims.

DESCRIPTION OF THE PREFERRED EMBODIMENTS

Figure 1:
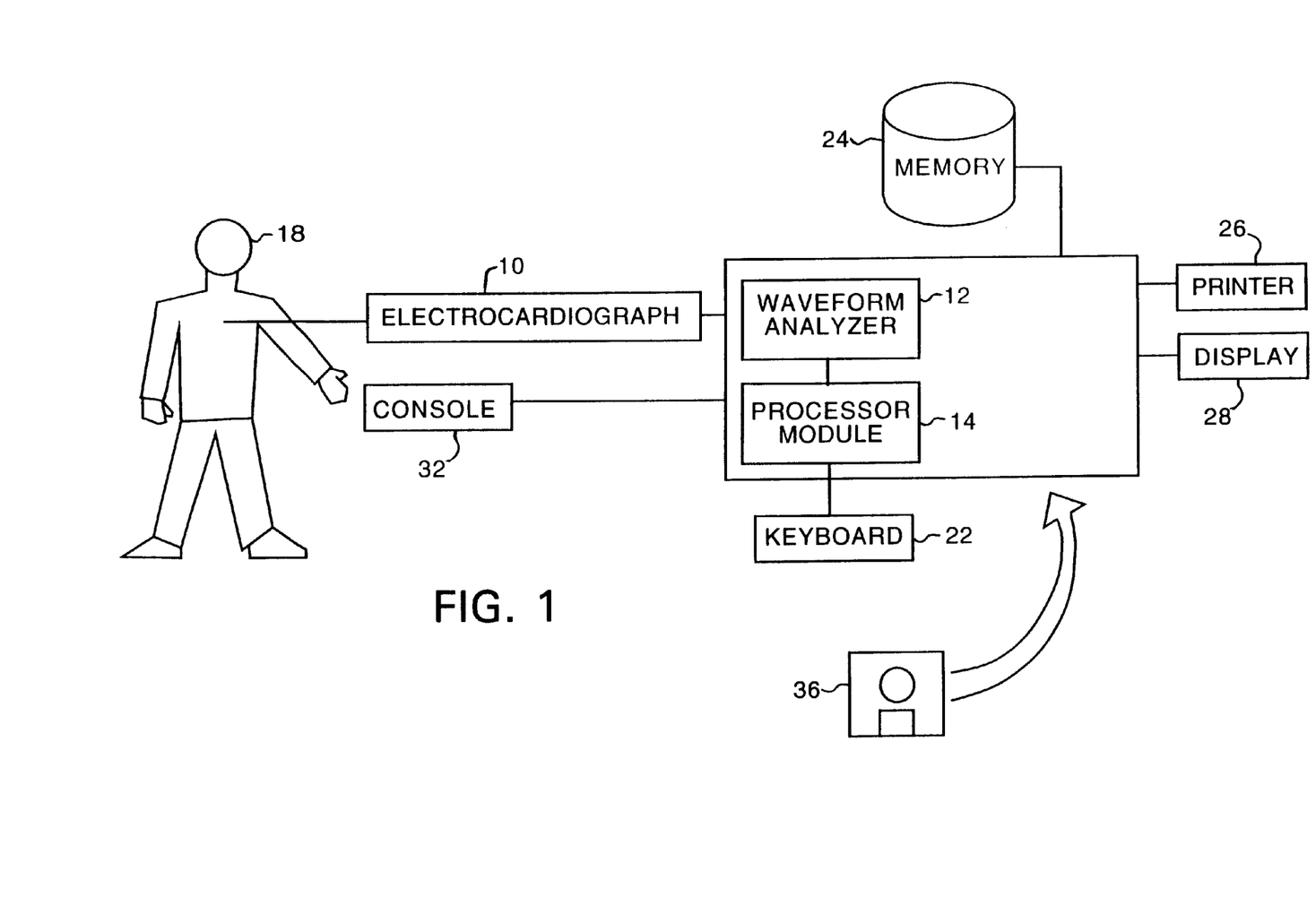
FIG. 1 is a block diagram of a diagnostic system which computes and presents an array of conditional probabilities of acute cardiac ischemia.

Referring to FIG. 1, a predictive instrument constructed in accordance with the invention includes a 12-lead electrocardiograph 10, a waveform analyzer 12, and a programmed processor module 14. Electrocardiograph 10 is connected to a patient 18 and produces a set of ECG waveforms for the patient. Waveform analyzer 12 is programmed to analyze the ECG waveforms and recognize the presence of certain characteristics that are particularly indicative of the cardiac condition of the patient, e.g. the presence and elevation or depression of S-T segments, the presence Q waves, and the presence of elevated, depressed or inverted T-waves. The particular characteristics which the waveform analyzer is programmed to recognize depend upon the function that is performed by the predictive instrument which in turn determines the set of clinical variables that are required to perform that function. Processor module 14 uses the output of waveform analyzer 12 in conjunction with other clinical information about the patient that has been entered by a physician through a keyboard 22 and is programmed to compute a probability that the patient has a life-threatening cardiac condition. According to an important aspect of the present embodiment, processor module 14 is also programmed to generate and display a hierarchical array of conditional probabilities which guide the physician in selecting the most appropriate diagnostic test or sequence of tests to perform on the patient to increase the certainty of the medical diagnosis.

The programs that are described herein are typically presented on a computer-readable medium, e.g. a CD-ROM or floppy disk 36. The program is then read into or loaded into the processor module or computer.

Figure 2:
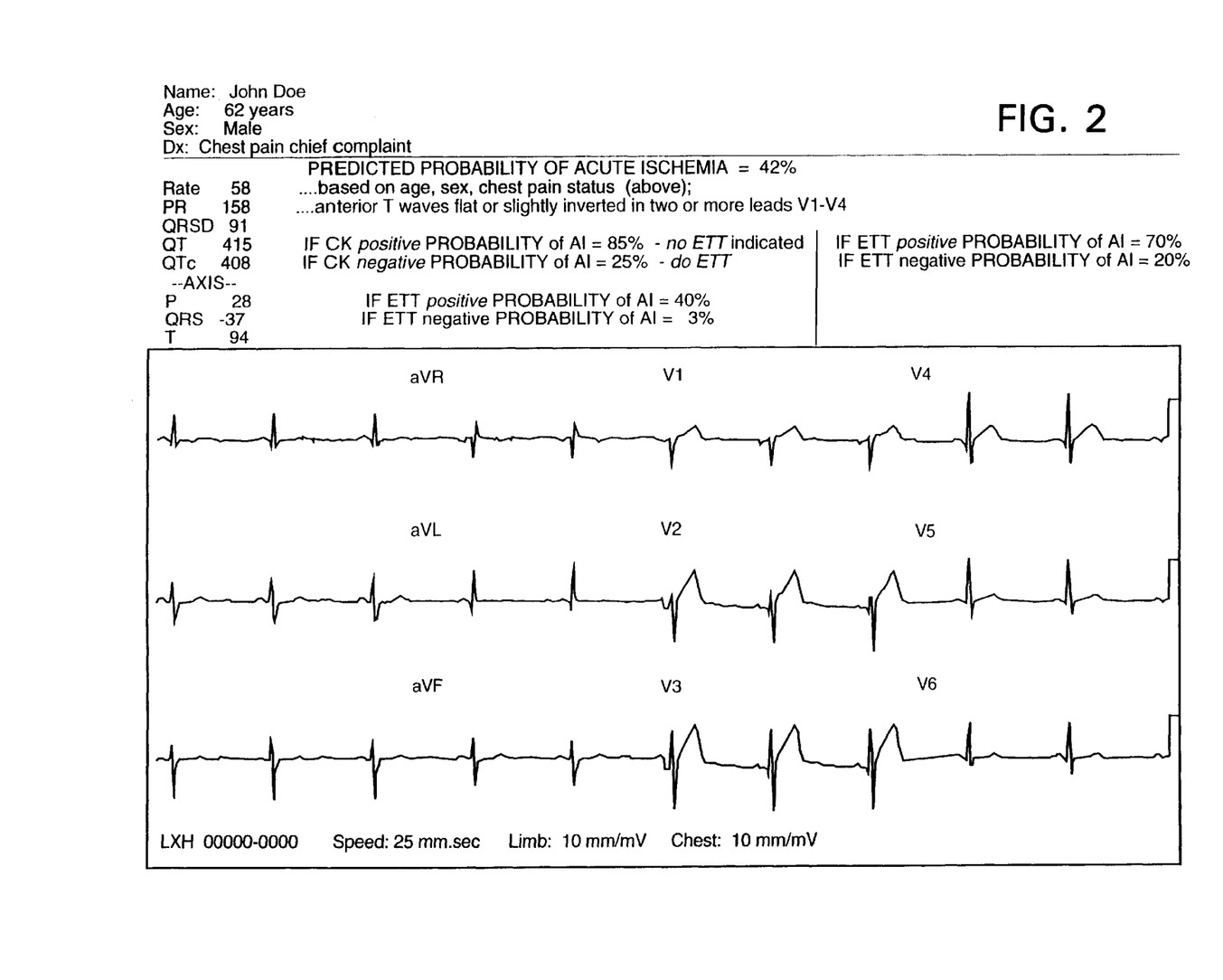
FIG. 2 is an example of a printout from the system illustrated in FIG. 1.

In the described embodiment, the processor module generates two sets of conditional probabilities, which are shown in FIG. 2. The first set includes two levels with the top level presenting the conditional probabilities for a CK (creatine kinase) blood test and the bottom level presenting conditional probabilities for an ETT (Exercise Tolerance Test), assuming that the CK blood test produced negative results. The second set simply presents the conditional probabilities for a ETT test given the results of the preceeding ECG and CK tests.

The processor module displays the computed probabilities in a form and manner that is designed to be most useful to the physician using the predictive instrument. Typically, the results are printed across the top of the ECG waveform trace output that is also generated by the electrocardiograph so that a permanent record of them is generated for the patient's file and so that they are available in a convenient readily accessible form for the physician. Alternatively, or in addition, the results can be displayed in some other fashion such as through the video monitor that is part of the instrument.

In this example, the significance of the information which is communicated to the physician is as follows. Based upon the monitored ECG waveform and the presenting information that is obtained from the patient, the computed probability of acute cardiac ischemia (ACI) is 42%. In other words, among the people that were represented in the database that was used to generate the regression equation, 42% of those people who had similar characteristics were actually experiencing ACI.

Besides presenting this initial information, the report also presents the physician with guidance regarding what further tests to perform on the patient in order to most effectively and efficiently decide whether the patient's likelihood of acute cardiac ischemia is such that he or she should be admitted to the hospital or allowed to go home. The guidance is in the form of the predicted conditional probabilities for each of twD tests that could be performed on the patient, namely, a CK blood test and an ETT. If a CK blood test is performed and the results are positive, the computed probability of ACI will increase to 85%. That would be high enough to suggest an admission without further testing but not clearly high enough to clearly mandate hospitalization. However, if the CK blood test results produce negative results, the probability will fall to 25%. The 25% is still high enough to justify continuing concern and to thus warrant further testing. If the ETT is then performed for the patient, assuming that the patient produced negative CK blood test results, the outcome of the ETT will change the computed probabilities in the manner shown. If the ETT is negative, the probability will fall to 3%, justifying a non-admission decision for the patient. Whereas if the ETT results are positive, the probability will increase to 40%, which probably warrants admitting the patient for further observations. So, before performing any tests on the patient beyond the initial examination and the ECG, the physician, by knowing what the potential diagnostic yield might be by the use of different tests, can be guided in both the choice of tests and also the ultimate decision.

As an alternative to the CK blood test as the first test, the report also presents conditional probabilities for an ETT (see information presented in upper right side of FIG. 2). In this case, the processor module determines that if an ETT is performed, a positive result will yield a predicted probability of 70% and a negative result will yield a predicted probability of 30%. In this particular example, the computed probabilities for this patient seem to indicate that performing the CK blood test as the first test will produce the most discrimination between a patient who should be admitted and one who can be allowed to go home.

Though shown as separate units, electrocardiograph 10 and waveform analyzer 12 are commercially available as a single unit. For example, Hewlett Packard makes the HP Pagewriter XLi which is a mobile unit that can be moved from one patient to the next. The Pagewriter XLi includes an internal computer that can be programmed to perform the appropriate waveform analysis. For example, it can be programmed to recognize and quantify the presence of key features within the ECG waveform. It can also be programmed to identify the location of a myocardial infarction (MI) based on the characteristics of the set of signals produced by the twelve monitoring leads. Besides performing the wave analysis functions, the computer within the unit can also be programmed to perform the functions of other components or modules within the system, e.g. the computations of the predictive instrument.

In the described embodiment, processor module 14 uses logistic regression-based equations for computing the probabilities that the patient is experiencing acute cardiac ischemia. For further descriptions of predictive instruments which are capable of computing probabilities of ACI or other medical problems and which can be used in connection with the present invention refer to the following patents, all of which are incorporated herein by reference: U.S. Pat. No. 4,957,115 by Selker, entitled Device for Determining the Probability of Death of Cardiac Patients"; U.S. Pat. No. 4,998,535 by Selker et al., entitled "Thrombolysis Predictive Instrument"; U.S. Pat. No. 5,277,188 by Selker, entitled "Clinical Information Reporting System"; and U.S. Pat. Nos. 5,501,229, 5,718,233 and U.S. Pat. No. 5,724,983, all three of which are by Selker et al., and are entitled "Continuous Monitoring Using A Predictive Instrument".

The logistic regression equations are of the following general form:

$$P = 100\left[1 - \frac{1}{1+e^z}\right]$$

where P is the probability of a particular medical outcome or diagnosis, and where z has the following general form:

$$z = b_0 + \Sigma b_i x_i.$$

In this equation, $b_0$ is a constant, and the $b_i$'s are coefficients of the explanatory variables $x_i$ which are included in the model. The variables that are used in the model will of course depend upon the particular medical outcome or diagnosis which is being evaluated. Some examples are presented below along with variables that would be included in the model.

Standard, well known regression techniques and other mathematical modeling may be employed to identify the most appropriate set of explanatory variables, namely, the $x_i$'s, and to determine the values of the coefficients of these variables. For a description of such techniques and examples of commercially available computer programs that implement them, see N.C. Cary in SUGI Supplement Library User's Guide, SAS Institute, p. 181–202, 1983, and L. Engelman, "PLR Stepwise Logistic Regression," BMDP Statistical Software, Chap. 14.5, pp. 330–334, BMDP publishers, Westwood, Calif. Of course, the precise set of explanatory variables that are identified and the predictive ability of the resulting logistic equation generally depends upon the quality of the underlying data that is used to develop the model. Such factors as the size and completeness of the database are often of significant importance. The selection of the relevant variables and the computation of the appropriate coefficients are well within the skill of an ordinary person skilled in the art.

Figure 3:
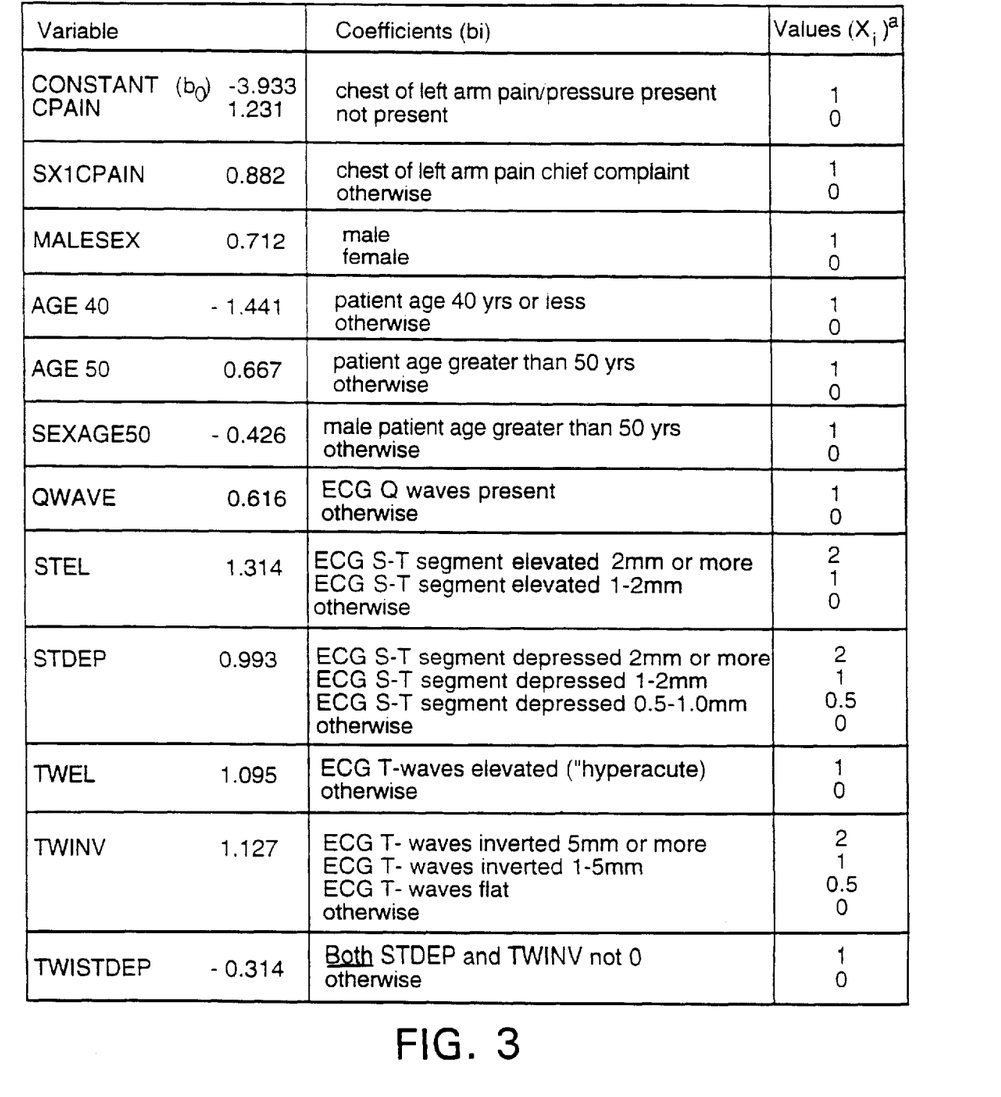
FIG. 3 presents the coefficients and variables of an example of a logistic regression equator used to predict a particular cardiac outcome, e.g. the probability of acute cardiac ischemia.

In the described embodiment, the variables which are used in this equation to compute what we shall refer to as the initial probability are shown in FIG. 3 along with the values of the coefficients and the values which the $x_i$'s can take for the different variables. Note that only the largest value for x is used per variable. Also ECG findings must be present in at least two leads, and S-T segment and T wave changes are "normal" if secondary to right or left complete bundle branch blocks, left ventricular hypertrophy, or a paced QRS. Only one type of abnormality is coded each for S-T segment and for T wave per patient (exclusive of TWISTDEP), use with elevation taking priority. Deviations are expressed in mm using the standard ECG scale of 1 mm=0.1 mV.

In the above-described embodiment of the present invention, each level of conditional probabilities is computed using a corresponding different logistic regression equation. Each regression equation is derived using the same approach that was used to derive the regression equation illustrated in FIG. 3. However, at least one additional explanatory variable is added to account for the test that is being modeled by the regression equation. In the equation which incorporates the CK blood test results, those test results are represented as an additional dichotomous variable (e.g. an additional $b_j x_j$ term in the regression equation). Similarly, in the equation which incorporates the ETT test results, those results are also represented by at least one additional dichotomous variable.

Figure 4:
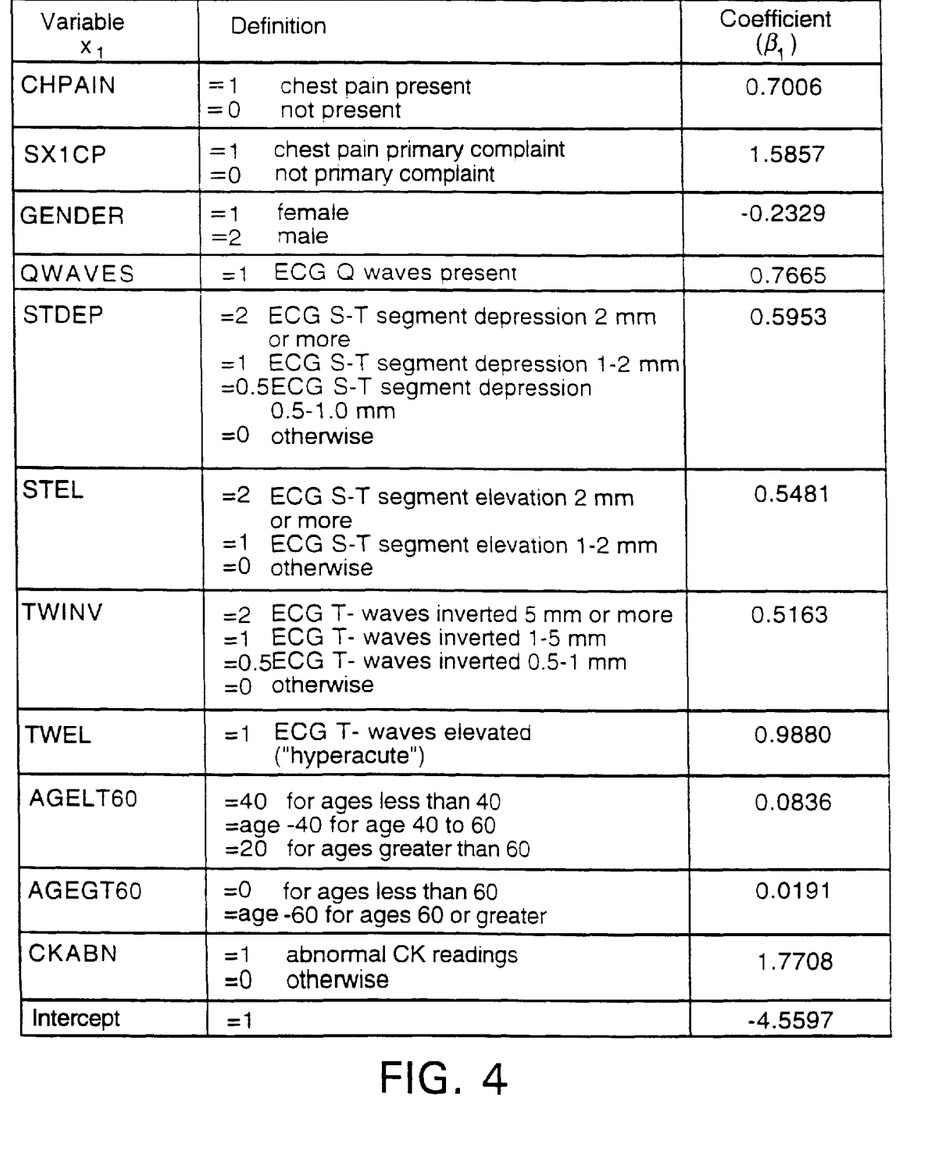
FIG. 4 presents the coefficients and variables of an example of a logistic regression equation used to compute a conditional probability, e.g. the probability of acute cardiac ischemia assuming that that a CK test results are available.

An example of the variables which would appear in the logistic regression equation which computes the conditional probabilities for the CK blood test and the coefficients for those coefficients is presented in FIG. 4. In that figure, the additional variable that accounts for the outcome of the CK test is referred to as CKABN. It takes on two values, namely, 1 for an abnormal CK reading and 0 for otherwise. The other variables are described in the figure. As indicated above, the processor module computes a probability for each value of the variable and reports those as the conditional probabilities.

Though we have described the test results as being dichotomous, they need not be modeled that way. For example, the CK blood test results can be modeled as producing three possible outcomes, e.g. positive, negative, and ambiguous. The same is true for many of the other variables that could be used in the regression equation to predict the patient's condition. Indeed, the variables could even be modeled to have more than three possible discrete outcomes or even to be a continuous variable that takes on values over a range of numbers.

The system operates in the following manner. When the patient is first connected to the system, the physician or other user enters the relevant clinical information about the patient. For example, if the predictive instrument is programmed to compute the probability of acute cardiac ischemia in accordance with the above model, the physician enters the following information about the patient: (1) name; (2) age; (3) sex; (4) whether the patient is experiencing chest or left arm pain; and (5) whether the patient's chief complaint is chest or left arm pain. After the physician has set up the system for a particular patient and connects the leads of the electrocardiograph to the patient, the physician causes the system to perform an initial ECG for the patient. In response, the waveform analyzer acquires and analyzes a current segment of the patient's ECG waveform. Typically, a 10–20 second segment of the patient's ECG is required by the waveform analyzer to perform its waveform analysis functions. In the present embodiment, the output of the waveform analyzer reports whether: (1) any Q waves are present; (2) whether the S-T segment is elevated or depressed and by how much; (3) whether the T-waves are elevated inverted or flat; (4) if the T-waves are elevated, by how much; and (5) whether both the STDEP and TWINV leads are non-zero.

Using the output of the waveform analyzer and previously entered values for other clinical variables, the processor module computes a probability that the patient has acute cardiac ischemia and the array of conditional probabilities that the system is configured to generate. This information is then printed on the top of the ECG printout in the manner described earlier.

The choice of the CK blood test and ETT was not meant to be limiting. There are other potential tests that could be included either in addition to cr as alternatives to the CK blood test and ETT. For example, other tests that could be performed include: other blood tests such as troponin and myoglobin and radionucleide imaging tests, such as Sestamibi scanning, and other forms of exercise stress tests, just to name a few. Also, there are other ways in which to display the array of conditional probabilities. We have described a simple presentation. But more a complex tree or multiple trees of conditional probabilities could be generated. The added conditional probabilities, however, present greater challenges in communicating the information to the physician in an effectively and readily understandable manner.

The logistic regression equations mentioned above are presented as merely illustrative of one way in which the cardiac condition and the probabilities can be modeled. There are a variety of statistical methods and algorithms that can be used for calculating the predicted probability of an adverse cardiac event or a life threatening cardiac condition. These include, for example, artificial feed-forward multi layer neural networks and classification trees. Although the procedures may differ among these various techniques, many of them may generally be expressed in terms of finding an optimal solution to the following general equation:

$$f^{-1}(\text{probability of event}) = \beta_0 + \sum_{i=1}^{K} \beta_i g_i(X_1, X_2, \ldots X_p),$$

where $f^{-1}$ and $g_i$ are general functions, the $X_n$'s (where $1 \leq n \leq p$) are the values of the independent input variables, and $\beta_0$ and $\beta_i$ (where $1 \leq i \leq K$) are model coefficients.

The standard logistic regression equation described earlier can be derived from the above equation. In addition an artificial network with a single hidden layer and an activation function "h" can be written as:

$$f^{-1}(\text{output}) = \beta_0 + \sum_{i=1}^{K} \left\{ \beta_i h \left( \sum_{j=1}^{p} \alpha_{ij} X_j \right) \right\}.$$

Other embodiments are within the following claims. Even though the computing the probability of acute cardiac ischemia was used as an example, this was not meant to limit the scope of the invention to only those systems which compute that particular probability. The invention also encompasses systems which monitor and compute any probability of a serious cardiac condition. In addition, the method by which the probability is not computed is not central to the invention. Any approach which attempts to model historical patient information to compute a probability of the patient having a serious cardiac condition based at least in part upon ECG information falls within the scope of this invention.

In addition, the diagnostic tool described above has applicability to many other medical problems beyond the above-described cardiac related problems. The extension to circumstances that are not cardiac related is straight forward. Such alternative embodiments would likely (but not necessarily) have a similar functional block diagram structure to that described above, except that a different diagnostic or monitoring instrument would be used in place of the electrocardiograph, and the system may or may not include a module which analyzes the output of the monitoring instrument before providing input to the predictive instrument portion.

The following are further examples of applications involving non-cardiac diagnoses or medical outcomes, along with their likely key clinical variables.

In the domain of vascular disorders, the regression equations for computing the probabilities of a pulmonary embolus would include among its key variables the same variables as listed above, and also heart rate and respiration rate, as well as a modification of the symptoms regarding the suddenness of onset, and also ECG variables related to right heart strain (e.g. relating to QRS complex and ST/T wave changes). Diagnostic tests for which conditional probabilities would be important would include pulse oximetry $P_aO_2$ (oxygen concentration in the blood) and echocardiogram evidence of pulmonary hypertension and/or right ventricular strain, and other blood tests.

In the domain of neurologic disorders, the regression equations for computing the probabilities of a cerebral hemorrhage (i.e., hemorrhagic stroke) would include among their key variables the patient's history of medications (e.g. anticoagulants, etc.), prior history of cardiac disorders that predispose to cerebral thrombosis (e.g. atrial fibrillation, valvular disease), and history of trauma to the head, as well as laboratory tests such as prothrombin time and partial thromboplastin time and platelet count, which are all measures of the clotting ability of the blood. They also include blood pressure, with emphasis on pulse pressure (i.e., a difference between the systolic and diastolic pressure). The most important additional diagnostic tests for which conditional probabilities would be useful would include CT and MRI scan evidence of stroke.

In the domain of general surgery, the regression equations for computing the probabilities of an intra-abdominal catastrophe (i.e., the need for emergency surgery) would include among their key variables the presence of abdominal pain, the patient's physical findings by the physician of so-called peritoneal signs (rigidity of the abdomen, no bowel sounds, etc.), monitor data such as temperature, heart rate, blood pressure, and potentially x-ray findings that reveal bowel gas pattern. Diagnostic tests for which conditional probabilities would be useful include tests for the complete blood count (CBC: including the white blood cell count, the red cell count (or hematocrit), and the platelete count), as well as tests for the erythrocyte sedimentation rate (ESR) and abdominal sonography.

In the domain of infectious diseases, the regression equations for computing the probabilities of sepsis (i.e., overwhelming infection that would require certain emergency treatments) would include among their key variables the patient's level of consciousness, specific complaints, and monitored physiologic measures such as blood pressure (especially low), heart rate (especially high), respiratory rate (especially high), body temperature (especially either unduly high or unduly low), ECG abnormalities (as not showing a contrary cardiac cause for derangements in heart rate, blood pressure, respiratory rate ard other findings in the form of an interaction term in the mathematical model) laboratory tests such as white blood court (either unduly high or unduly low), and other special blood tests typically available on-line from hospital clinical information systems. Also, other ongoing monitoring data relating to blood and other body fluid culture results, such as are typically available on electronic clinical information systems, are further important explanatory variables relating to the source of sepsis. Examples of additional tests on which conditional probabilities would be based would include blood interleukin levels, c-reactive protein, and pulse oximetry.

Each of the above diagnoses to be predicted have consequences in terms of clinical outcomes including, for example, mortality. Other outcomes that can be predicted by a predictive instrument include mortality due to acute myocardial infarction or congestive heart failure, as well as conditional outcomes such as are obtained from the thrombolytic predictive instrument (see U.S. Pat. No. 4,998,535). The use of this approach also applies to other non-cardiac conditions for which prediction of medical outcomes can be conditioned on the use of specific therapies.

The examples presented above are meant to be merely illustrative of the many ways in which the invention can be used to aid in the diagnosis of a patient's medical condition. It is not intended that the invention be limited to the few examples that were described here. In general, the invention covers any instrument which computes on the basis of a set of clinical features a probability of a medical outcome or diagnosis and an array of conditional probabilities associated with possible follow-up tests that could be performed.

By clinical features, it should be understood that we mean any data form that gives direct information about the clinical, i.e., the medical, state of the patient. As described above, some clinical features can be directly acquired in electronic form, such as heart rate and respiratory rate acquired by monitors, such as waveforms acquired by an electrocardiograph, such as oxygen saturation measured by a sensor attached to the patient's finger (pulse oximetry), and such as biochemical laboratory results. However, other clinical features can be obtained in other forms and in other ways as well. For example, as described above in connection with the use of the cardiac predictive instrument, direct questioning of the patient provides important clinical features, namely, whether or not the patient is having chest pain and whether chest pains are the chief complaint. Analogously, for a predictive instrument for predicting various respiratory diagnoses or outcomes, a relevant clinical feature would be an indication as to whether the patient has shortness of breath. These symptoms are linked to the relevant underlying medical processes and can, in combination with other clinical variables in the mathematical model, add important information. And in the case of a predictive instrument for predicting neurologic problems, relevant clinical features include indications as to whether the patient has a headache and/or neurologic symptoms. In addition, some sources of data are less directly connected to the patient but nevertheless still supply important clinical features. For example, sociodemographic data such as age and gender are obviously important, as was the case for the cardiac predictive instrument described above. In addition, other relevant clinical feature data is reflected in medical insurance claims, such as the mere performance of certain tests, the fact of hospitalization, the actual diagnostic code (e.g. the ICD9 Code), etc. A clinical feature is any piece of additional information about the patient, which when incorporated into a mathematical model predicts a given medical outcome.

A medical outcome or medical diagnosis, such as might be predicted by a predictive instrument, is defined in the following way. A medical outcome is the state of a patient defined in medical terms, typically described in the context of a particular constellation of presenting symptoms and clinical features. In practice, the outcome is selected to be clinically meaningful to the care of the patient. Therefore, an important medical outcome for a patient with a heart attack is mortality. For a person with respiratory failure, it is also mortality but it is also long-term respiratory disability, which might be defined, for example, as lack of ability to do activities of daily living due to shortness of breath as well. For a person with neurologic presenting symptoms, an important medical outcome is preservation of normal mental function as well as mortality.

There is overlap between the concept of medical outcomes and medical diagnoses. For example, when a decision has to be made about a patient, before the clinician can evaluate the likely ultimate outcome, the clinician must first consider the specific medical diagnosis or family of diagnoses that the patient has which require attention. Thus, a diagnosis is, in a sense, an intermediate "outcome". For a person coming to the emergency department with chest pain and/or other signs and symptoms, the first question on the clinician's mind is, what is the diagnosis? If the diagnosis, i.e., the ongoing medical/clinical process, is acute cardiac ischemia (i.e., occlusion of a coronary artery), then this requires treatment to prevent its potential downstream outcomes from occurring (e.g., death) and that treatment is very different from what would be used if the diagnosis is costocondritis (inflammation of the joints of the sternum), stomach ulcer, or some other cause of the symptoms. Moreover, for all the medical conditions alluded to above, there are an array of tests that could be performed on the patient and thus it would be very helpful to provide guidance to the physician in selecting from among the possibilities the one or more tests that would provide the most information for the particular patient.

From the above, it should be apparent that the invention can be used with a wide variety of patient monitoring devices including, for example, heart rate monitors, respiratory rate monitors, bioanalyzers, blood oximeters, and fetal monitors, just to name a few.

What is claimed is:

1. A method for evaluating a medical condition of a patient, said method comprising:
   monitoring one or more clinical features of a patient;
   based on the monitored features, computing a primary probability of a medical outcome or diagnosis;
   computing a plurality of conditional probabilities for a selected diagnostic test, said conditional probabilities including a first probability of the medical outcome or diagnosis assuming the selected diagnostic test produces a first outcome and a second probability of the medical outcome or diagnosis assuming the selected diagnostic test produces a second outcome; and
   displaying the computed primary probability as well as the plurality of computed conditional probabilities to a user as an aid to determining whether to administer the selected diagnostic test to the patient.

2. The method of claim 1 wherein the step of monitoring comprises monitoring EKG-related characteristics of the patient, wherein the computed primary probability is a probability of a cardiac problem, and wherein the selected diagnostic test is selected from the group consisting of a CK blood test, an ETT, a stress test, and Sestamibi scanning test.

3. The method of claim 1 further comprising computing a second plurality of conditional probabilities for a second selected diagnostic test, said second conditional probabilities including a first probability of the medical outcome or diagnosis assuming the second selected diagnostic test produces a first outcome and a second probability of the medical outcome or diagnosis assuming the second selected diagnostic test produces a second outcome.

4. The method of claim 1 further comprising computing a second plurality of conditional probabilities for a second selected diagnostic test, said second plurality of conditional probabilities assuming a particular outcome of the first-mentioned selected diagnostic test, said second conditional probabilities including a first probability of the medical outcome or diagnosis also assuming the second selected diagnostic test produces a first outcome and a second probability of the medical outcome or diagnosis also assuming the second selected diagnostic test produces a second outcome.

5. A method for determining a diagnostic test plan for a patient, said method comprising:

monitoring EKG-related characteristics of the patient;

based on the measured characteristics, computing a primary probability of a cardiac problem;

computing a plurality of conditional probabilities for a selected diagnostic test, said conditional probabilities including a first probability of cardiac problem assuming the selected diagnostic test produces a first outcome and a second probability assuming the selected diagnostic test produces a second outcome; and displaying the computed primary probability as well as the plurality of computed conditional probabilities to a user as an aid to determining whether to administer the selected diagnostic test to the patient.

6. A diagnostic apparatus for use with a patient, said apparatus comprising:

a monitoring device which during use monitors one or more clinical features of the patient;

an output device; and a predictive instrument receiving input from the monitoring device and programmed to: (1) compute therefrom a primary probability of a medical outcome or diagnosis based on the monitored one or more clinical features; (2) compute a plurality of conditional probabilities for a selected diagnostic test, said plurality of conditional probabilities including a first probability of said medical outcome or diagnosis assuming the selected diagnostic test produces a first outcome and a second probability of said medical outcome or diagnosis assuming the selected diagnostic test produces a second outcome; and (3) display the computed primary probability along with the plurality of computed conditional probabilities on the output device.

* * * * *